US010374340B2

(12) United States Patent
Cook et al.

(10) Patent No.: US 10,374,340 B2
(45) Date of Patent: Aug. 6, 2019

(54) COMPACT MULTI-LINE CONNECTOR

(71) Applicant: Technical Services for Electronics, Inc., Minneapolis, MN (US)

(72) Inventors: Ryan Cook, Prior Lake, MN (US); David Wandler, Necedah, WI (US)

(73) Assignee: Technical Services for Electronics, Inc., Minneapolis, MN (US)

( * ) Notice: Subject to any disclaimer, the term of this patent is extended or adjusted under 35 U.S.C. 154(b) by 0 days.

(21) Appl. No.: 15/898,720

(22) Filed: Feb. 19, 2018

(65) Prior Publication Data
US 2018/0183159 A1 Jun. 28, 2018

Related U.S. Application Data

(63) Continuation of application No. PCT/US2017/020268, filed on Mar. 1, 2017.
(Continued)

(51) Int. Cl.
*H01R 12/53* (2011.01)
*A61B 5/00* (2006.01)
(Continued)

(52) U.S. Cl.
CPC ............ *H01R 12/53* (2013.01); *A61B 5/0422* (2013.01); *A61B 5/6852* (2013.01);
(Continued)

(58) Field of Classification Search
CPC ...... H01R 12/53; H01R 12/721; H01R 13/62; H01R 13/62988; H01R 13/62994;
(Continued)

(56) References Cited

U.S. PATENT DOCUMENTS 3,727,169 A * 4/1973 Crane ................ H01R 12/724
439/274
5,667,514 A * 9/1997 Heller ................ A61B 17/3403
604/160

(Continued)

FOREIGN PATENT DOCUMENTS

CN 103151631 A 6/2013
WO 2010011753 A1 1/2010
(Continued)

OTHER PUBLICATIONS

International Search Report and Written Opinion of international application PCT/US17/20268 dated Sep. 15, 2017.

*Primary Examiner* — Eun Hwa Kim
(74) *Attorney, Agent, or Firm* — Eggink & Eggink; Anthony G. Eggink; Katrina M. Eggink

(57) ABSTRACT

A multi-line electrical assembly that includes a multi-line cable (14), including a multiplicity of insulated conductive wires (59); and a multi-line electrical plug (16), physically connected to the cable. The plug has a housing (56) and a plurality of spaced-apart printed circuit boards (PCBs, 48), housed in the housing and having a first end (47) that is connected to the cable and having a second end (46), separated from the first end. Further, the PCBs bear a plurality of conductive traces (50), at least some of the traces being electrically connected to the wires proximal to the first end. The traces terminate proximal to the second end.

21 Claims, 8 Drawing Sheets

Related U.S. Application Data

(60) Provisional application No. 62/327,080, filed on Apr. 25, 2016.

(51) Int. Cl.
*H01R 12/72* (2011.01)
*H01R 24/60* (2011.01)
*A61B 5/042* (2006.01)
*H01R 13/622* (2006.01)
*H01R 13/625* (2006.01)

(52) U.S. Cl.
CPC ......... *A61B 5/6858* (2013.01); *H01R 12/721* (2013.01); *H01R 13/622* (2013.01); *H01R 24/60* (2013.01); *A61B 2562/0209* (2013.01); *A61B 2562/182* (2013.01); *A61B 2562/222* (2013.01); *A61B 2562/227* (2013.01); *H01R 13/625* (2013.01); *H01R 2201/12* (2013.01)

(58) Field of Classification Search
CPC . H01R 2201/12; A61B 5/0422; A61B 5/6852; A61B 5/6858; A61B 2562/227
See application file for complete search history.

(56) References Cited

U.S. PATENT DOCUMENTS

| | | |
|---|---|---|
| 6,540,550 B2 | 4/2003 | Chang |
| 6,652,322 B2 | 11/2003 | Ito |
| 7,094,086 B2 | 8/2006 | Teicher |
| 7,540,766 B2 | 6/2009 | Makinson et al. |
| 2001/0012726 A1 | 8/2001 | O'Neal et al. |
| 2003/0171035 A1 | 9/2003 | Yoo |
| 2004/0033711 A1 | 2/2004 | Loveless et al. |
| 2006/0144613 A1* | 7/2006 | Buck .................... H01B 7/0892 174/113 R |
| 2013/0244456 A1* | 9/2013 | Sakamoto .......... A61B 1/00124 439/81 |
| 2013/0296729 A1* | 11/2013 | Datta ...................... A61B 5/02 600/515 |
| 2014/0217571 A1 | 8/2014 | Ganesan et al. |
| 2015/0357734 A1 | 12/2015 | Copper et al. |
| 2016/0043509 A1* | 2/2016 | Reeves ................ H01R 13/631 439/374 |

FOREIGN PATENT DOCUMENTS

| | | |
|---|---|---|
| WO | 2010057735 A2 | 3/2010 |
| WO | 2016022678 A1 | 2/2016 |

* cited by examiner

COMPACT MULTI-LINE CONNECTOR

RELATED APPLICATION

This application is a continuation of international application number PCT/US17/20268 filed on Mar. 1, 2017, which itself claims benefit of provisional application U.S. Ser. No. 62/327,080 filed on Apr. 25, 2016, which are incorporated by reference as if fully set forth herein.

TECHNICAL FIELD

The present invention is in the field of electrical connectors. More specifically it is in the field of high contact density electrical connectors.

BACKGROUND ART

As biological measurement and monitoring systems become more complex, the desired number of electrical conductive paths into and out of catheters and other patient monitoring devices and equipment, increases. A catheter that includes an array of electrophysiological mapping electrodes, for example, may include multiple electrical signal lines, in order to produce precise imagery of an interior portion of the body. At some point, the catheter must be connected to a further cable, or to a device, thereby necessitating a multi-line or multi-position connector. A few difficulties have limited the number lines that can be accommodated with a connector. First there is the difficulty of constructing a connector with many different connection points, which are typically pins and sockets, for a great many different lines. It appears that typical high contact density electrical connectors have a maximum number of positions between 60 and 80 contacts.

Three more requirements create difficulties. First, there is the need for wiping action, as the connection is made and disengaged. That is, the plug portion of the connector must wipe against the socket portion, in order to wipe away oxidation that forms between instances of use. In the familiar two prong plug used in most American homes and offices, the two prongs slide past the socket contacts while being plugged in, and then while being plugged out. This causes enough oxide to be wiped off so that in almost all cases a robust electrical contact is made. But it also requires somewhat more force than would otherwise be necessary, both in the act of plugging in and plugging out. The second requirement is that the insertion force be low enough so that a person can easily perform these functions. When multiplied many times for a multi-line connector, this force can amount to an insurmountable barrier to use.

The third requirement is that the connector must be able to survive intact from a sterilization cycle through a steam autoclave, ethylene oxide sterilization, gamma sterilization, or other common medical device sterilization procedures. Many materials used in familiar connectors would be destroyed when exposed to such sterilization conditions and atmospheres. All of the materials used must be able to survive intact through sterilization cycles, and the construction best serves the needs of users if it does not present recesses in which microbial life could survive through the process.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a multi-line electrical assembly that includes a multi-line cable, including a multiplicity of insulated conductive wires; and a multi-line electrical plug, physically connected to the cable. The plug has a housing and a plurality of spaced-apart printed circuit boards (PCB), housed in the housing and having a first end that is connected to the cable and having a second end, separated from the first end. Further, the PCBs bear a plurality of conductive traces, at least some of the traces being electrically connected to the wires proximal to the first end. The traces terminate proximal to the second end.

In a second separate aspect, the present invention may take the form of an electrical connector assembly that includes a socket having a plurality of socket electrical contacts. Also, a plug, which is advanced in a forward direction in order engage to the socket, and having a forward-most front and a rear, opposed to the front. The plug includes a housing and a set of printed circuit boards, each one having a set of traces terminating in forward-positioned plug electrical contacts, at least some of which are connected to further conductors that exit from the rear of the plug. Finally, the plug electrical contacts and the socket electrical contacts are arranged and configured to slide into contact to one another as the plug is advanced in a forward direction into the socket.

In a third separate aspect, the present invention may take the form of a catheter assembly that includes a catheter having a distal portion adapted to be inserted into a human or animal body and that further includes electrical signal lines and has a proximal portion supporting the distal portion and the electrical signal lines, and that also has a proximal end. An electrical connector plug is fixed to the proximal end and has a housing and at least one printed circuit board (PCB), housed in the housing and that has a first end that is connected to the cable and a second end, separated from the first end. The PCB bears a plurality of conductive traces, at least some of the traces each being electrically connected to one of the electrical signal lines, proximal to the first end, the traces terminating proximal to the second end. Further, the catheter assembly is made entirely of materials that can withstand an autoclave cycle without being damaged.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

BEST MODES OF CARRYING OUT THE INVENTION

Figure 1:
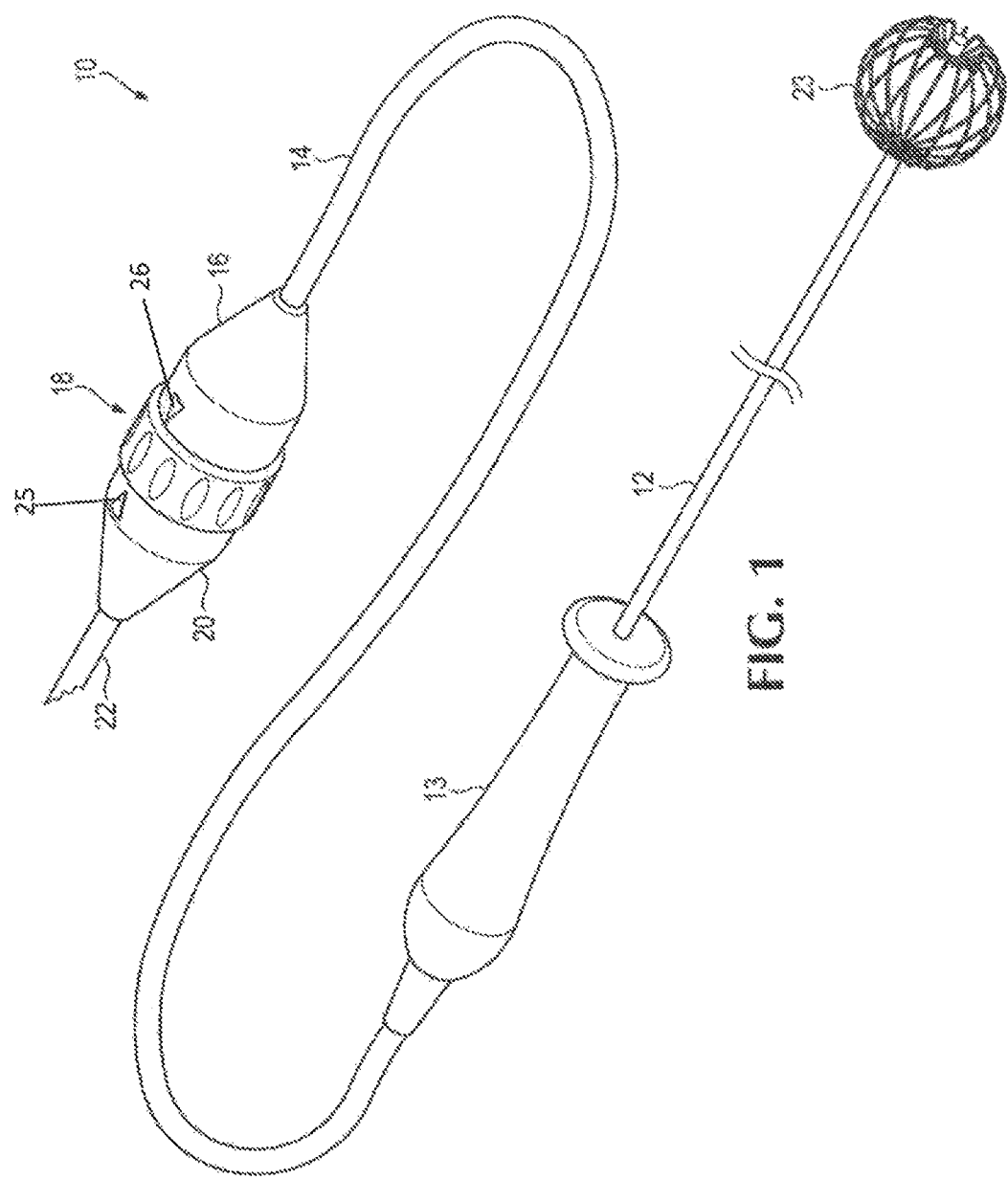
FIG. 1 depicts a catheter assembly connected to a mated connector assembly via electrical signal cables.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring to FIG. 1, in a preferred embodiment a catheter assembly 10 according to the present invention, includes a catheter 12 having a handle 13, a distal electrical signal cable 14 terminating in a plug 16 that is part of a connector assembly 18, which further includes a socket 20, and finally a proximal electrical signal cable 22. In an alternative preferred embodiment (not shown), socket 20 is mounted on the panel of a device for driving catheter 12 receiving and processing and/or displaying signals generated in catheter 12. In a further alternative embodiment cable 14 terminates in socket 20, which connects to plug 16, either leading into proximal cable 22 or as modified plug 16', being mounted on the panel of a device FIG. 2B). In one preferred embodiment catheter 12 includes an electrophysiological mapping array having over 100 imaging elements. In the embodiment shown catheter 12 includes an electrophysiological mapping head 23, but many other embodiments of catheters exist, for other medical purposes, as many catheter applications exist that can benefit from a large number of signal lines.

Figure 2A:
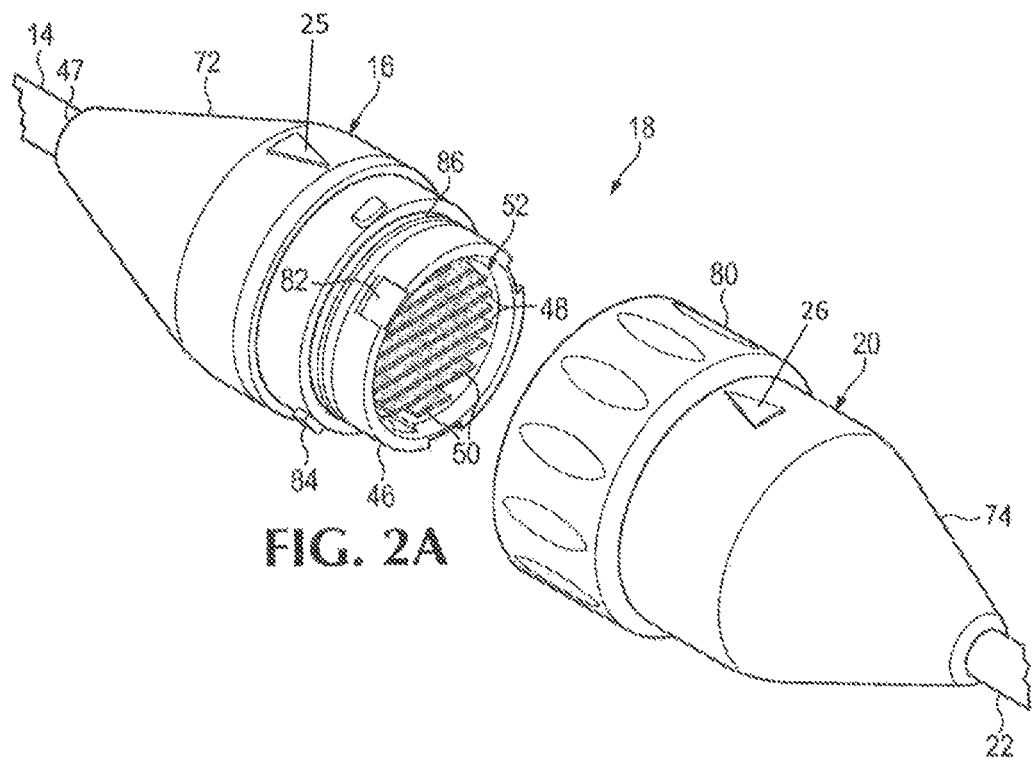
FIG. 2A illustrates the unmated plug component of the connector assembly of FIG. 1.
Figure 3:
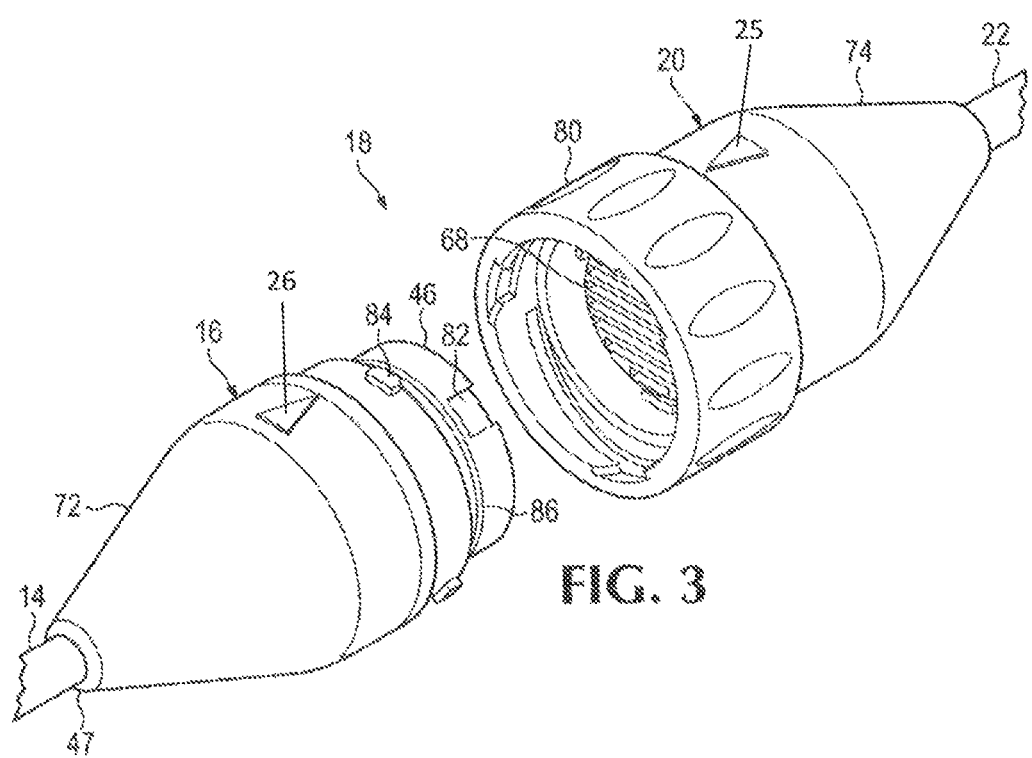
FIG. 3 shows the inner lattice of the unmated receptacle component of the connector assembly of FIG. 1.
Figure 4:
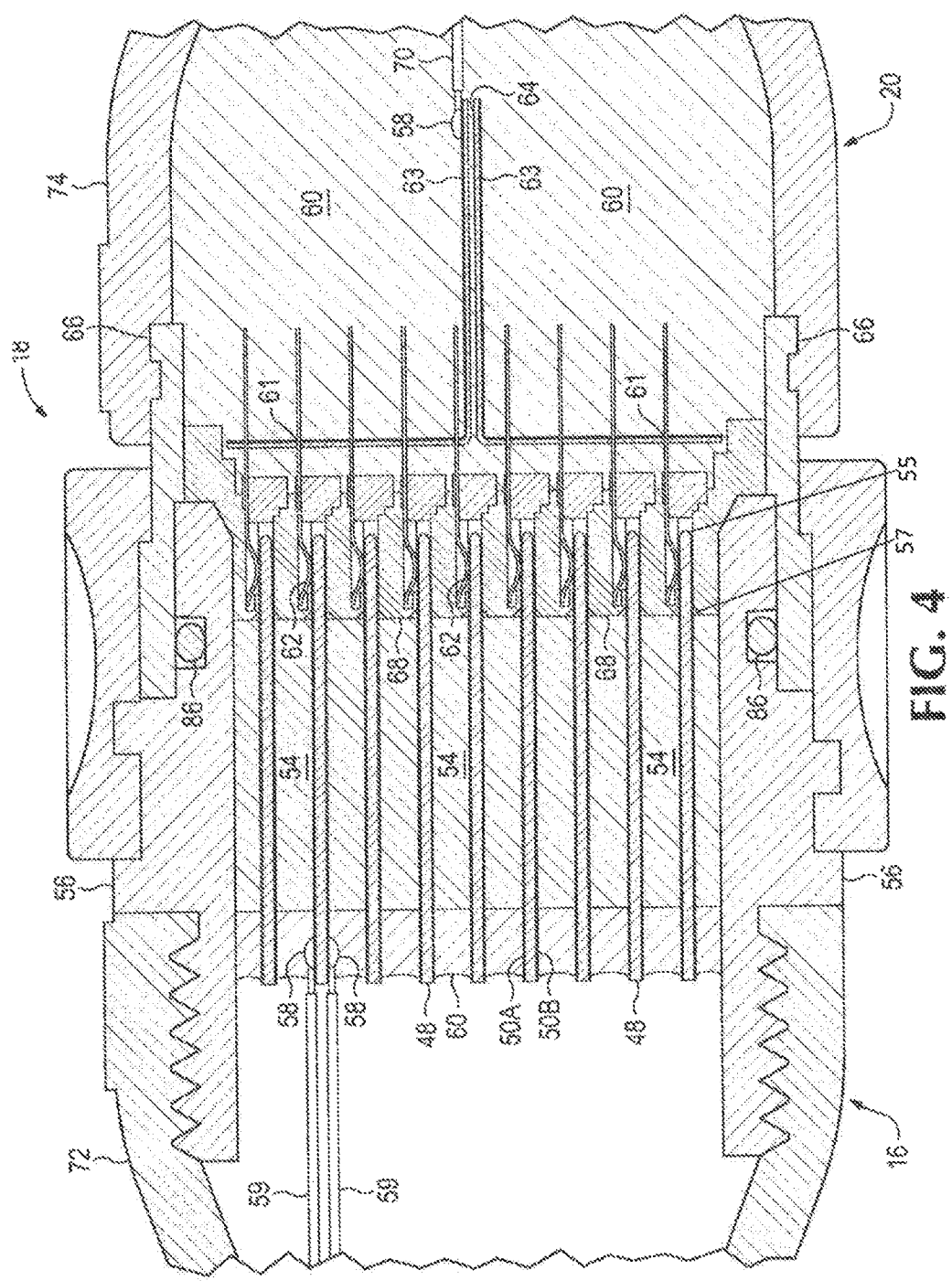
FIG. 4 is a cross-section of the mated connector assembly of FIG. 1.

Referring to FIGS. 2A, 3 and 4, in one preferred embodiment a connector assembly 18, includes a plug 16 and a socket 20. The plug 16 has a front end 46 and a back end 47, thereby defining a forward direction from hack end 47 to front end 46. Further, plug 16 includes a plurality of printed circuit boards (PCBs) 48, each of which include a multiplicity of conductive traces 50 generally extending from back to front of each PCB 48. The PCBs 48 have tapered frontal edges 55 and a stack 52 of PCBs 48 is shown held together by spacing elements 54, and is press fit into a cylindrical plug housing 56. The back side of traces 50 are each generally connected by solder 58 to some conductor of cable 22. In some embodiments, some traces 50 will be left unused, whereas in other embodiments all traces 50 will be connected to a conductor of cable 22. Conductors 59 of cable 14 may include center conductors and shields of coaxial cables, wires, and shields that are not, part of a coaxial cable), These solder connections are potted after stack 52 is press fit into housing 56, with housing 56 and spacing elements 54 helping to hold the liquid putting material in place as it cures, to create a layer of cured potting material 60. Crimping and welding may alternatively be used for these connections, In one embodiment, a housing, otherwise like housing 56, forms a portion of a catheter handle, otherwise like handle 13.

Figure 2B:
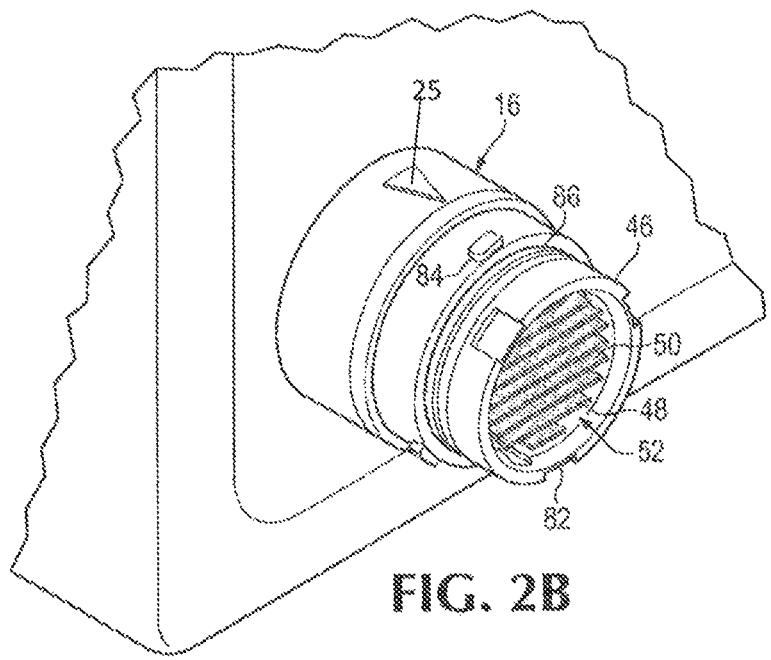
FIG. 2B illustrates an unmated plug component, like that of FIG. 2A, but mounted into a panel.

In a preferred embodiment, defining the top to coincide with the orientation of FIGS, 2A, 3 and 4, the top and bottom PCBs 48 are more narrow than the middle PCBs, so that stack 52 is roughly circular in cross-section, thereby matching the circular or cylindrical interior of plug housing 56. FIG. 2B shows a plug 16' similar to plug 16 of FIG. 2A, but forming a part of a panel of a device, such as a signal processing and display assembly. In this embodiment, it is cable 14, from the medical device, that terminates in a socket, that attaches to plug 16'. In an alternative embodiment, a socket similar to socket 20 is mounted in the panel of a signal processing and display device, and cable 14 terminates in plug 16, which mates with this socket.

A socket 20 generally includes a leaf spring contact 62 for each trace 50 of plug 16. As plug 16 and socket 20 are moved together, each leaf spring 62 slides over a trace 50, to form an electrical connection. The wiping action of this contact removes oxide that might otherwise prevent the formation of a robust electrical connection. Leaf springs are formed of a beryllium copper alloy that is formed in sheets, die cut and bent, to form a series of individual leaf springs 62, which are then threaded through vias 61 formed through conductive traces 63 on flex circuits 64. The leaf springs 62 are press fit into a receptacle housing 66, that includes a front protective lattice 68 with tapered entries 57, that permits entrance of the frontal edges 55 of PCBs 48, while generally protecting leaf springs from unintended contact from outside elements when the socket 20 is free of the plug 16. Wires 70 are soldered to a grid of contacts. Both housing 56 and housing 66 may be made of a broad range of materials, including polymeric materials and metals. In an alternative preferred embodiment (not shown) either the socket or the plug is connected to a wireless transceiver, for sending signals from a sensor suite to a wireless receiver.

Figure 5:
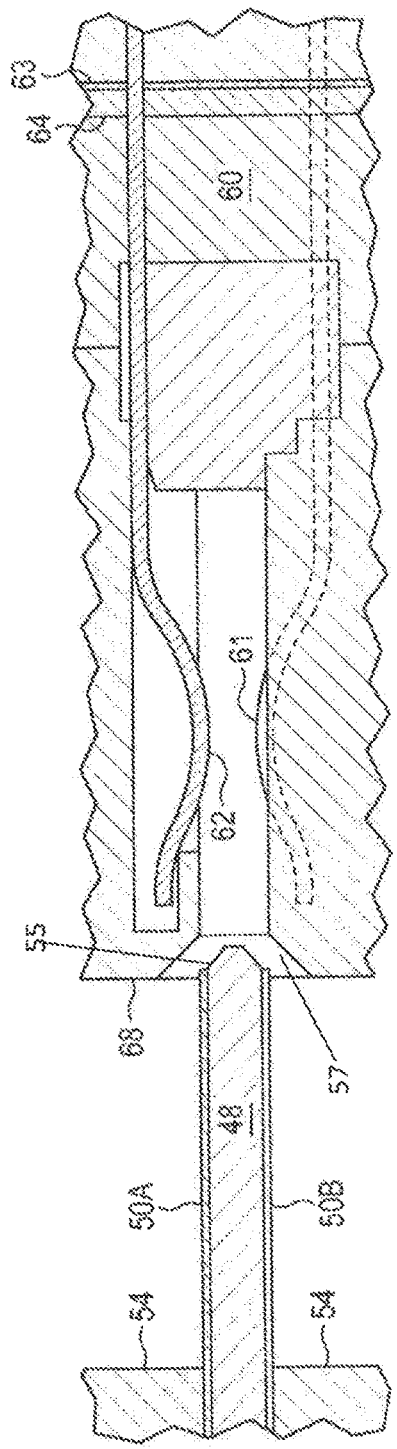
FIG. 5 is a cross-section of unmated traces and leaf springs of connector assembly of FIG. 4.
Figure 6:
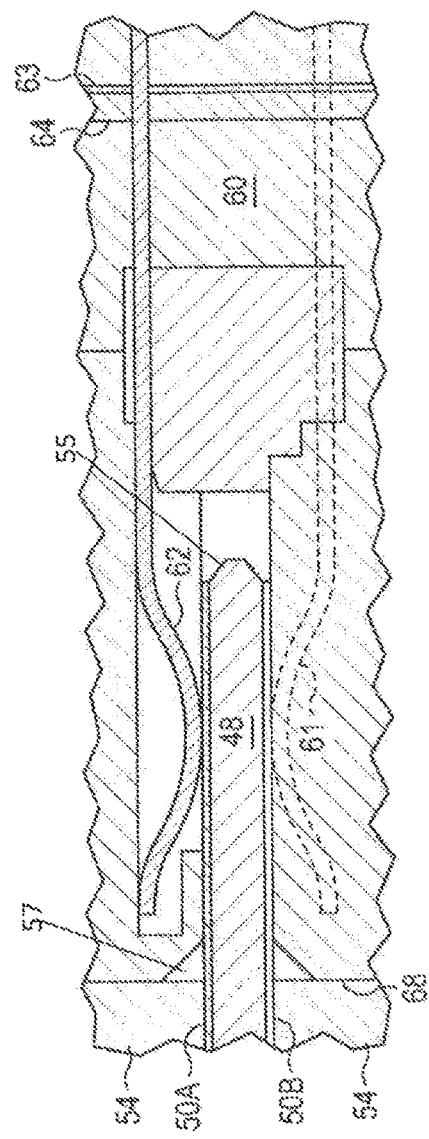
FIG. 6 is a cross-section of mated traces and leaf springs of the connector assembly of FIG. 4

Referring to FIGS. 5 and 6, both sides of each PCB 48 support traces 50, with top traces 50A and bottom traces 50B being interleaved, with a bottom trace 50B, as shown in FIGS. 5 and 6 being slightly displaced in the dimension orthogonal to the section plane shown, so that it does not appear in cross-section as does top trace 50A. Likewise, bottom leaf spring 62B, which contacts conductive trace 50B is shown as being displaced from the section plane, and partially obscured by lattice 68. As part of assembly a plug strain relief housing 72 and a receptacle strain relief housing 74 are molded onto plug housing 56 and leaf spring holder 66, respectively. Housing 72 and 74 prevent forces applied to cable 14 or cable 22 from causing wires 59 from pulling on PCBs 48 or wires 70 from pulling on flex circuits 64 and potentially damaging or breaking the solder joints.

Socket 20 further includes a freely rotatable locking ring 80 that has three evenly spaced, inwardly facing channels 82 each of which accepts a rectangular post 84 on plug 16. Channels 82 each include a helical portion so that as ring 80 is rotated counter-clockwise (facing the front of socket 20) plug 16 and socket 20 are drawn together. This provides mechanical advantage to overcome the insertion force, thereby permitting a human user to electrically connect plug 16 and socket 20, without having to apply a degree of force that might strain some users. In a preferred embodiment, the insertion force is less than 3 lbs, and in a more specific preferred embodiment it is less than 1.5 lbs, including the mechanical advantage provided by the locking ring. An 0-ring 86 positioned on the plug 16 seals the joined connector to an IP67 level of protection, in a preferred embodiment, socket 20 includes a return spring (not shown), which moves the locking ring 80 to an unlocked position, ready to he locked onto posts 84, when socket 20 is not in use, In an additional alternative embodiment, a plug, otherwise like plug 16, is equipped with a locking ring, similar to ring 80, and a socket, otherwise like socket 20 includes mating posts 84. Visual alignment guides 25 and 26 may be included, such as the triangles shown in the drawings, to inform the user of when the plug 16 and socket 20 are aligned so as to be mated together. Also, a visual guide may be provided on the lock ring 80, to inform the user of when the lock ring is in a rotational position to mate for channels 82 to mate with posts 84. In another alternative, there is no lock ring. In this alternative, the plug and socket may have any transverse shape. Various devices for gaining mechanical advantage may be used, or no device for gaining mechanical advantage may be used.

Figure 7:
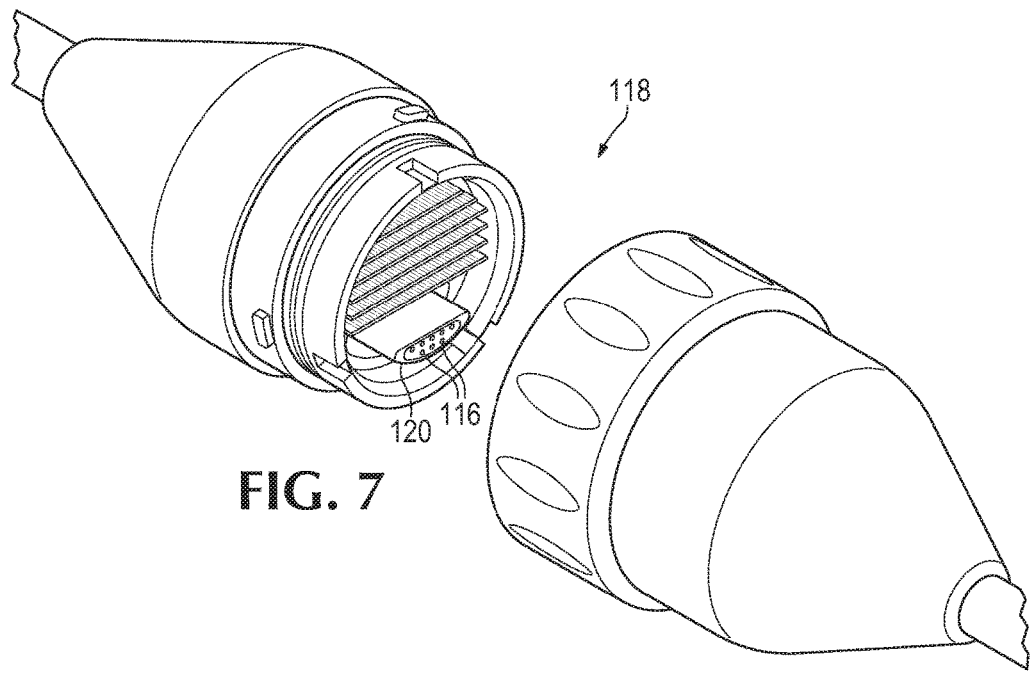
FIG. 7 depicts the plug component of an unmated connector assembly having a protruding element and sockets in place of several stacks of printed circuit boards.
Figure 8:
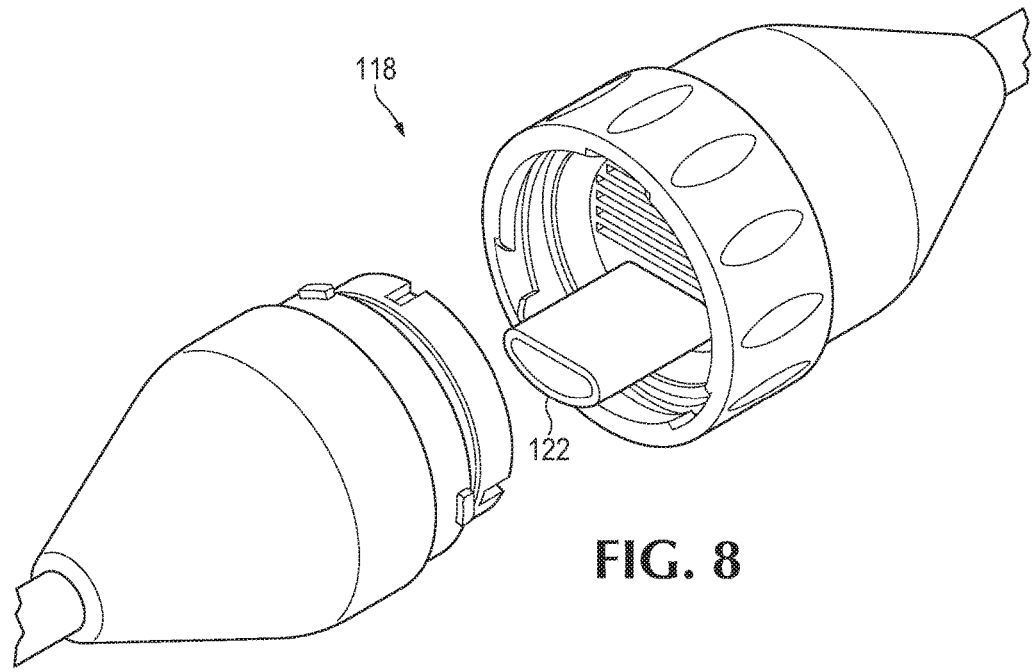
FIG. 8 depicts the receptacle of the unmated connector assembly of FIG. 7 having a protruding sleeve to accept a protruding element.
Figure 9:
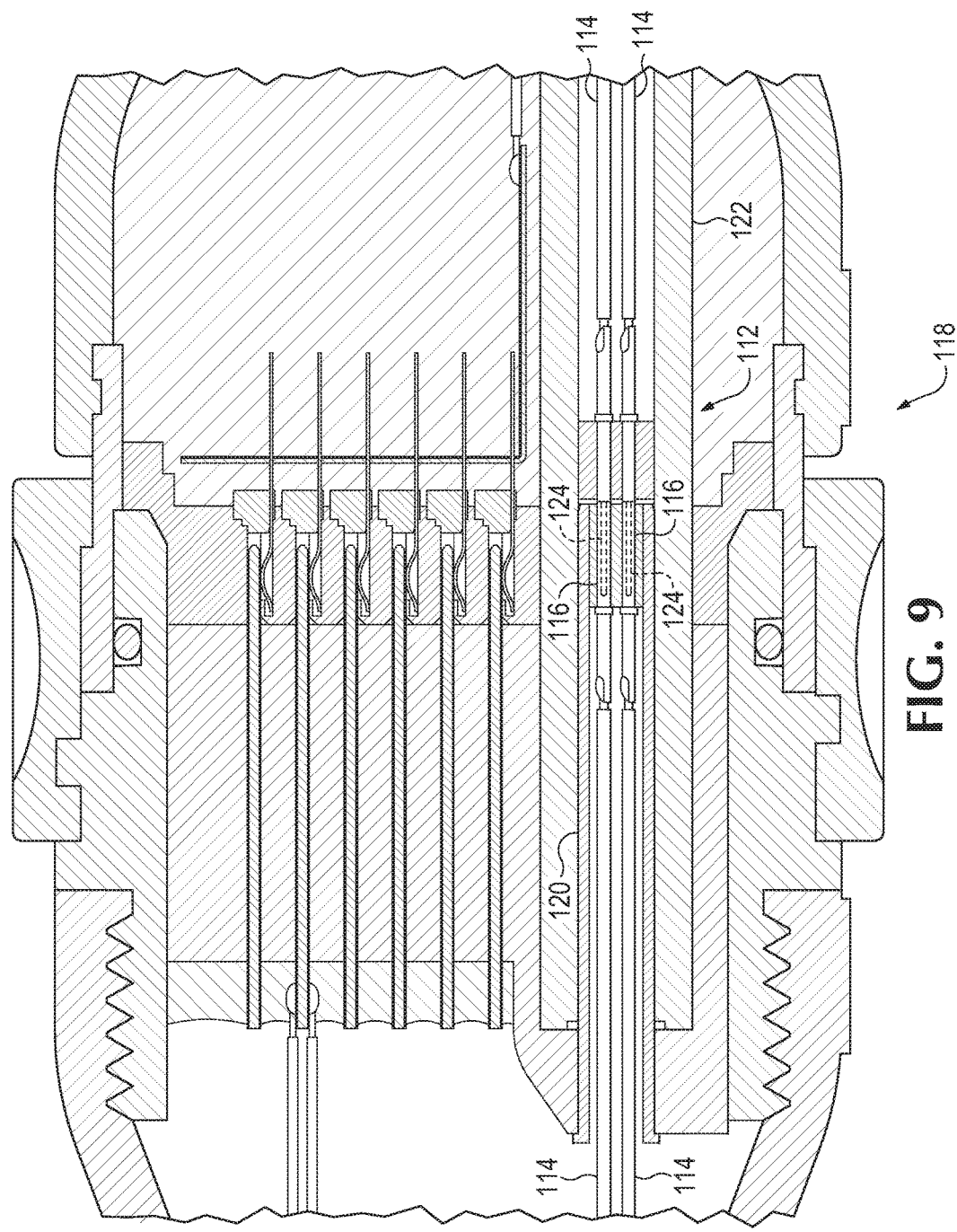
FIG. 9 is a cross-section of the mated connector assembly of FIGS. 7 and 8.

Referring to FIGS. 7-9, in a second preferred connector embodiment 118, the PCB 48 portion of plug 16 and mating portion of socket 20 are the same as for connector 18, except for that the bottom two (and top one) PCBs are missing and replaced by a subassembly 112 adapted to permit the connection of conductive lines 114 specially adapted to protect very delicate signals that must be shielded against magnetic fields having frequency of less than 150,000 Hz (including a constant magnetic field). Signals of this delicate nature may originate from a catheter designed to detect electrostatic emissions of the heart from inside a heart chamber, for cardiac mapping. Such signals could easily be corrupted by being placed on the traces of the PCBs 48, either from larger signals on neighboring traces or from a signal from outside connector 18. Accordingly these signal lines are terminated in a set of sockets 116 defined in a protruding element 120, that mates into a protruding sleeve 122, electromagnetically shielding a set of pins 124 that mate into sockets in a standard manner. Sleeve 122 includes a layer of material having a relative permeability of greater than 1,000, such as a mu-metal, as well as other shielding to prevent corruption from higher frequency signals. In an alternative preferred embodiment, the entire plug and socket assemblies are covered with a material having a relative permeability of greater than 1,000.

Figure 10:
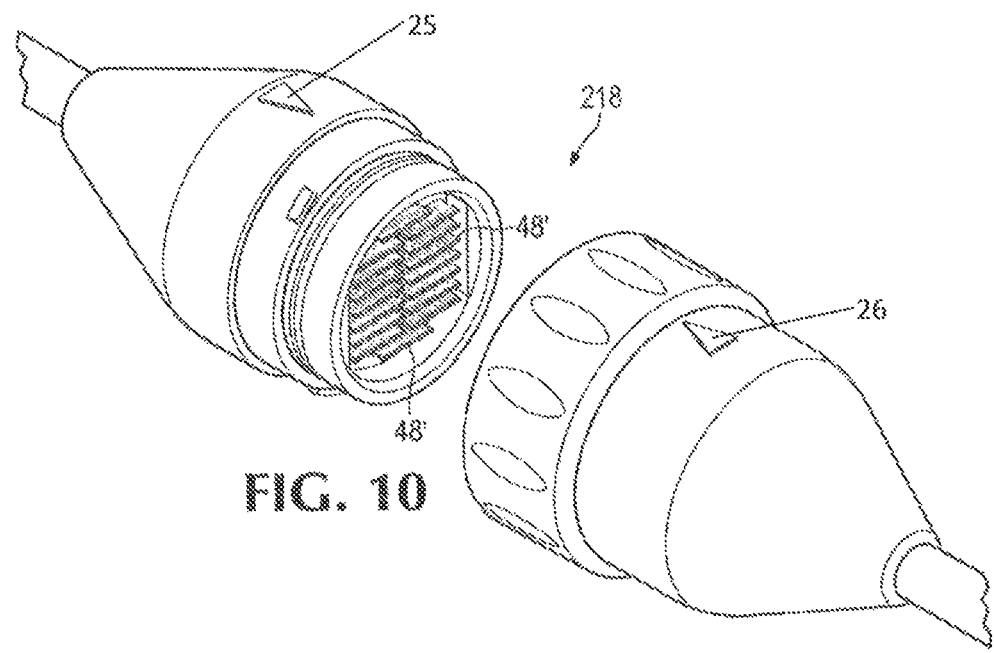
FIG. 10 depicts a plug component of an unmated connector assembly having stacks of identically-sized printed circuit boards.
Figure 11:
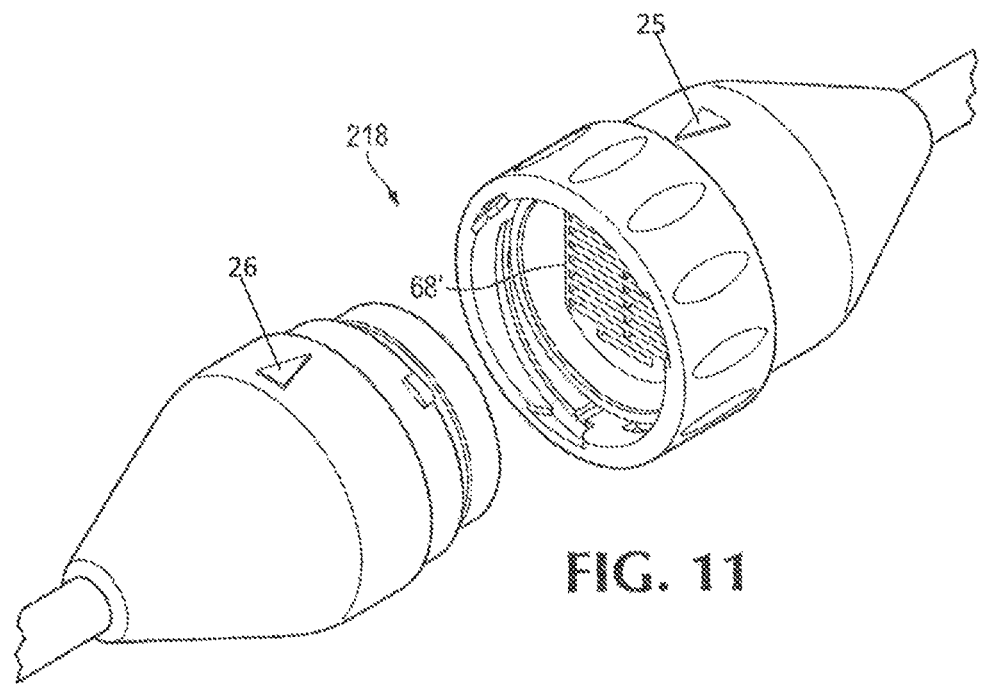
FIG. 11 shows the receptacle of the unmated connector assembly of FIG. 10 having a lattice structured to accept the printed circuit boards of the plug component of FIG. 10.

Referring to FIGS. 10 and 11, a third preferred connector embodiment 218 is just the same as the first connector 18 except for that the PCBs 48' used in connector 218 are all the same size. The leaf spring contacts and the lattice 68' are arranged to matingly engage with plug 16. By using PCBs that are mutually identical, manufacturing costs are reduced.

In preferred embodiments all of the materials of catheter assembly 10 and, if considered separately, plug 14, are made of materials that can withstand an autoclave cycle and other methods of sterilization, such as low-temperature, hydrogen peroxide gas plasma sterilization (marketed under the trademark STERRAD®), dry heat sterilization, gamma radiation sterilization and Ethylene Oxide sterilization. For example, the use of industry designation FR-4 material, or some other fiberglass for PCBs 48 or 48'. In a preferred embodiment connector 18 has an outer diameter of 35 mm and includes over 200 electrical connections. Embodiment 218 has an outer diameter of 50 and includes over 250 electrical connections. In addition to the card edge connectors, other types of connectors may be included in a connector, according to the present invention, to connect a broad range of signal types. Further, a connector, in accordance with the present invention, may be constructed to permit the passage of a fluid, such as air or a liquid, light, further electrical connectors or a wireless signal, may also be passed between plug and socket in either direction.

INDUSTRIAL APPLICABILITY

The present invention finds industrial applicability in the manufacture and supply of electrical connectors. Some embodiments find industrial applicability in the supply of medical equipment and parts for medical equipment.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A multi-line electrical catheter assembly, comprising:
 (a) a multi-line cable, including a multiplicity of insulated conductive wires, having a first end and a second end, opposed to said first end;
 (b) a multi-line electrical plug, physically connected to said first end of said cable and including:
  (i) a cylindrical housing adapted to electrically engage a socket;
  (ii) a plurality of spaced-apart printed circuit boards (PCB), housed in said cylindrical housing and having a first end that is connected to said cable and having a second end, separated from said first end, said PCBs bearing a plurality of conductive traces, at least some of said plurality of traces being electrically connected to said wires proximal to said first end, said plurality of traces terminating proximal to said second end, said PCBs further having tapered ends at said second ends; and
  (iii) a plurality of spacing elements to hold said PCBs in the spaced apart orientation, said plurality of spacing elements and PCBs being fixed in said cylindrical housing; and wherein said PCBs are all identical, and are arranged in rows, with intermediate rows having two PCBs, but having two outermost rows, each having a single PCB only; and
 (c) a catheter, attached to said second end of said multi-line cable, and including sensing elements that generate signals on said wires of said cable.

2. The assembly of claim 1, wherein said second end of said PCBs extends outward from said plurality of spacing elements, wherein said plug includes a strain relief housing extending from said cylindrical housing and wherein said cylindrical housing has a visual alignment guide and wherein said visual alignment guide is for alignment with a visual alignment guide of the socket.

3. The assembly of claim 1, wherein at least some of said wires are shielded by a shield, and wherein at least some of said shields are connected to one of said traces.

4. The assembly of claim 3, wherein a coaxial cable with a center connector is provided and wherein at least one of said shielded wires is the center conductor of the coaxial cable.

5. The assembly of claim 1, wherein said plug is a panel-mounted plug.

6. The assembly of claim 1, wherein said catheter includes an electrophysiological mapping electrode array.

7. The assembly of claim 1, wherein said assembly can withstand an autoclave cycle, hydrogen peroxide gas plasma sterilization, dry heat sterilization, gamma radiation sterilization and ethylene oxide sterilization.

8. The assembly of claim 1, wherein said wires are soldered to said traces at soldering joints, and wherein said soldering joints are covered by a layer of potting material that contacts said spacing elements.

9. A multi-line electrical catheter assembly, comprising:
(a) a multi-line cable, including a multiplicity of insulated conductive wires, said multi-line cable having a first end and a second end; and
(b) a multi-line electrical plug, physically connected to said first end of said cable and including:
(i) a cylindrical housing adapted to electrically engage a socket, said cylindrical housing having a visual alignment guide;
(ii) a plurality of spaced-apart printed circuit boards (PCB), housed in said cylindrical housing and having a first end that is connected to said cable and having a second end, separated from said first end, said PCBs bearing a plurality of conductive traces, at least some of said plurality of traces being electrically connected to said wires proximal to said first end, said plurality of traces terminating proximal to said second end, said PCBs further having, tapered second ends;
(iii) a plurality of spacing elements to hold said PCBs in the spaced apart orientation and said plurality of spacing elements and PCBs being fixed in said cylindrical housing, wherein said PCBs are arranged in a stack and wherein the top and bottom PCBs in said stack are more narrow than the middle PCBs in said stack; and
(c) a catheter assembly, and including a catheter at an end of said electrical cable opposed to said plug, said catheter including sensing elements that generate signals on said wires of said cable, wherein said assembly can withstand an autoclave cycle, hydrogen peroxide gas plasma sterilization, dry heat sterilization, gamma radiation, sterilization and ethylene oxide sterilization.

10. The assembly of claim 9, wherein said second end or said PCBs extends outward from said spacing elements, wherein said stack of PCBs is press fit in said cylindrical housing and wherein said multi-line electrical plug includes a plug strain relief housing.

11. The assembly of claim 9, wherein at least some of said wires are shielded by a shield, and wherein at least some of said shields are connected to one of said traces.

12. The assembly of claim 11, wherein a coaxial cable with a center connector is provided and wherein at least one of said shielded wires is the center conductor of the coaxial cable.

13. The assembly of claim 9, wherein said plug is a panel-mounted plug.

14. The assembly of claim 9, wherein a catheter is provided, said catheter being, attached to said second end of said multi-line cable and wherein said catheter includes an electrophysiological mapping electrode array.

15. The assembly of claim 9, wherein said wires are soldered to said traces at soldering joints, and wherein said soldering joints are covered by a layer of potting material that contacts said spacing elements.

16. The assembly of claim 9, further being a catheter assembly, and including a catheter at an end of said electrical cable opposed to said plug, said catheter including sensing elements that generate signals on said wires of said cable.

17. A compact multi-line electrical connector assembly for connecting a biological measurement and monitoring system with a catheter assembly, comprising:
(a) a socket having a socket housing and a plurality of socket electrical contacts;
(b) the catheter assembly including sensing elements and a plug, wherein said plug is advanced in a forward direction in order to engage said socket, and having a forward-most front and a rear, opposed to said front, said plug including;
(i) a plug housing;
(ii) a set of printed circuit boards, each printed circuit board having a set of traces terminating in forward-positioned ping electrical contacts, at least some of which are connected to further conductors that exit from said rear of said plug; and
(iii) a plurality of spacing elements to hold said set of printed circuit boards in a spaced apart orientation, said plurality of spacing elements and printed circuit boards being fixed in said plug housing, wherein said PCBs are arranged in a stack and wherein the top and bottom PCBs in said stack are more narrow than the middle PCBs in said stack;
wherein said plug electrical contacts and said socket electrical contacts being arranged and configured to slide into contact with one another as said plug is advanced in a forward direction into said socket; and
wherein said printed circuit boards of said plug have tapered frontal ends and wherein said socket includes tapered front entries for the aligned engagement with said tapered front ends of said printed circuit boards of said plug.

18. The assembly of claim 17, wherein said socket electrical contacts are leaf spring contacts.

19. The assembly of claim 17, wherein said socket housing and said plug housing are cylindrical in structure, each having an outside surface and each having a visual alignment member thereon.

20. The assembly of claim 19, wherein a lock ring is provided and wherein said plug and said socket are engaged by way of said lock ring, said lock ring having a first half that defines a set of helical grooves and a second half that defines a set of tabs sized, shaped and spaced apart to fit into said set of helical grooves, so that when said first half and second half are rotated relative to each other, said tabs are drawn pushed along said helical grooves, causing said plug and socket to be drawn together, so that said plug electrical contacts connect to said socket electrical contacts.

21. The assembly of claim 20, wherein said tabs are keyed to said grooves, to prevent incorrect relative positioning of plug and socket.

* * * * *